(12) United States Patent
Crew

(10) Patent No.: US 11,510,864 B2
(45) Date of Patent: Nov. 29, 2022

(54) REMOVABLE HAIR COLORING COMPOSITION AND METHODS OF USE THEREOF

(71) Applicant: Melissa Joy Crew, Irvine, CA (US)

(72) Inventor: Melissa Joy Crew, Irvine, CA (US)

(*) Notice: Subject to any disclaimer, the term of this patent is extended or adjusted under 35 U.S.C. 154(b) by 0 days.

(21) Appl. No.: 17/095,973

(22) Filed: Nov. 12, 2020

(65) Prior Publication Data

US 2021/0137821 A1    May 13, 2021

Related U.S. Application Data

(60) Provisional application No. 62/933,772, filed on Nov. 11, 2019.

(51) Int. Cl.
| | | |
|---|---|---|
| *A61Q 5/10* | (2006.01) | |
| *A61K 8/92* | (2006.01) | |
| *A61Q 5/06* | (2006.01) | |

(52) U.S. Cl.
CPC .............. *A61K 8/922* (2013.01); *A61Q 5/065* (2013.01)

(58) Field of Classification Search
CPC . A61Q 5/10; A61Q 5/065; A61Q 5/12; A61K 2800/4324; A61K 2800/882; A61K 2800/88; A61K 2800/884; A61K 8/922; A61K 8/92

USPC ............................................................... 8/405
See application file for complete search history.

(56) References Cited

U.S. PATENT DOCUMENTS

| | | | | |
|---|---|---|---|---|
| 8,105,393 | B2* | 1/2012 | Suddaby ................ | A61K 8/84 8/405 |
| 2005/0058618 | A1* | 3/2005 | Evans .................... | A61K 8/60 424/70.14 |
| 2005/0282924 | A1* | 12/2005 | Katogi ................. | H01L 21/563 522/170 |
| 2007/0124872 | A1* | 6/2007 | Eliu ....................... | A61K 8/49 8/406 |
| 2011/0083284 | A1* | 4/2011 | Suddaby ................ | A61Q 5/10 8/405 |

* cited by examiner

*Primary Examiner* — Eisa B Elhilo
(74) *Attorney, Agent, or Firm* — Sandra Poteat Thompson; Finlayson Toffer

(57) ABSTRACT

Removable hair coloring compositions are described herein that include: at least one hair color composition or compound; and at least one sealing component or compound, wherein at least one of the at least one hair color composition or compound, or the at least one sealing component or compound can be physically dissolved, physically removed, or a combination thereof when mixed with at least one natural oil. In some embodiments, removable hair coloring compositions further include at least one preparation stage component or compound.

16 Claims, 3 Drawing Sheets

Figure 3

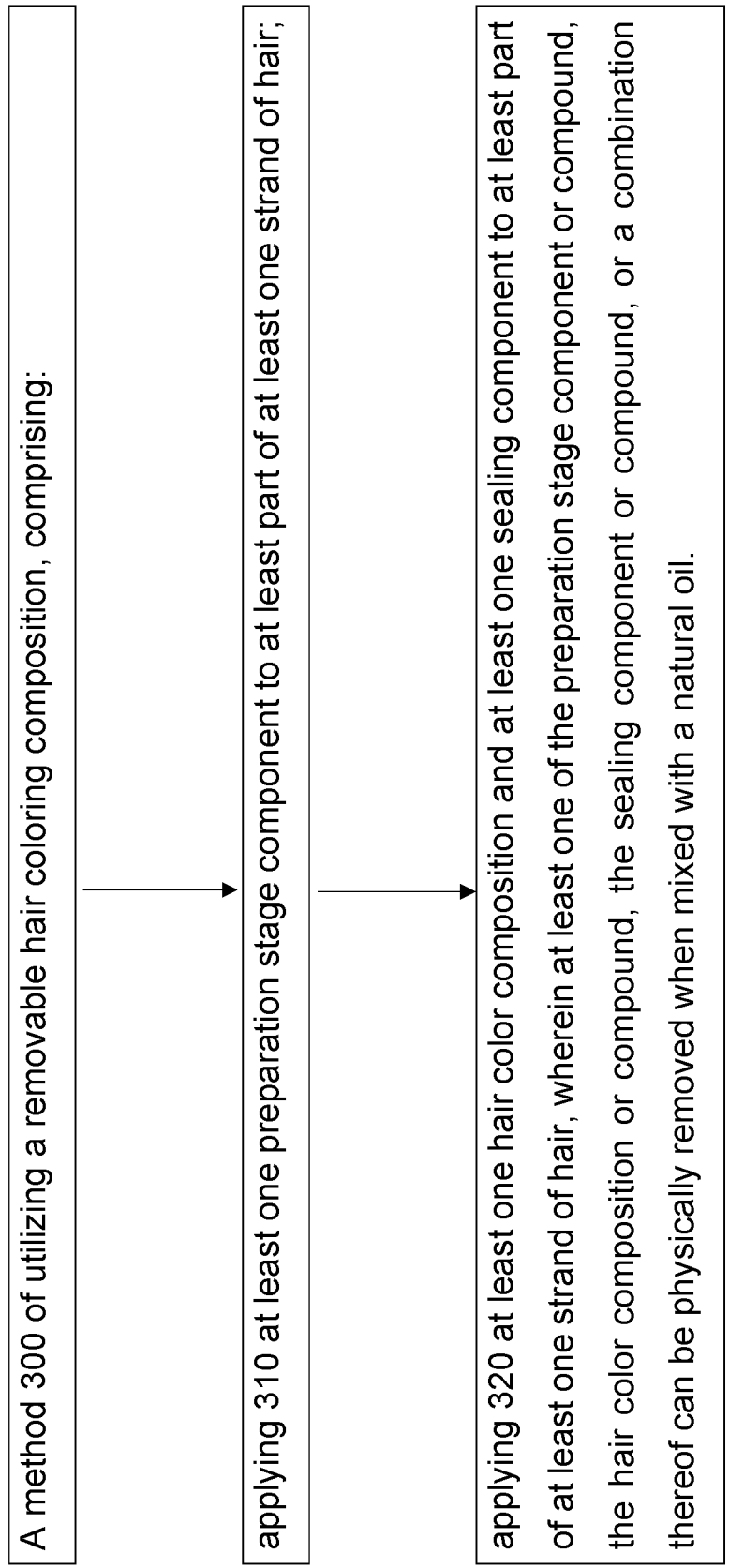

A method 300 of utilizing a removable hair coloring composition, comprising:

applying 310 at least one preparation stage component to at least part of at least one strand of hair;

applying 320 at least one hair color composition and at least one sealing component to at least part of at least one strand of hair, wherein at least one of the preparation stage component or compound, the hair color composition or compound, the sealing component or compound, or a combination thereof can be physically removed when mixed with a natural oil.

ns that are designed to be removable and the methods of
REMOVABLE HAIR COLORING COMPOSITION AND METHODS OF USE THEREOF This United States Utility application claims priority to U.S. Provisional Patent Application Ser. No. 62/933,772, which was filed on Nov. 11, 2019 and which is incorporated by reference in its entirety herein.

FIELD OF THE SUBJECT MATTER

The field of the subject matter is hair coloring compositions that are designed to be removable and the methods of their use.

BACKGROUND

The business of hair coloring and treatment for both men and women is large and full of wildly different options. For example, a consumer can go to a salon and spend hundreds of dollars on professional hair treatment that ranges from root touch-ups to highlighting to completely changing the color of that consumer's natural hair color. Another consumer can sign up for a monthly subscription service to hair coloring and root touch-ups that are delivered to his or her door for a recurring fee. And yet another consumer can walk into a local drug store or convenience store and buy a box of hair coloring for a few dollars and apply it at home.

At the low end of the hair coloring spectrum, there are a number of temporary color applications and shampoos that allow a consumer to try a new color or apply color to his or her hair, wherein it will last until the next shampoo wash. These types of color applications take the form of powders, creams, sprays, shampoos, and combinations thereof. They may come off on the consumer's hands or clothing after application and are not ideal for a modern consumer who is active and on-the-go.

There are a lot of haircare clients with grey hair that who spend a considerable amount of time retouching their grey hair. For example, a woman with dark hair will have a noticeable streak of grey hair near the scalp, as it starts to grow. It takes time and money to keep the grey hair concealed. They don't want to go grey but feel frustration as soon as they see the grey start popping through. This can occur as early as a week after a color retouch, depending on how much grey they have and how fast their hair grows. This type of hair growth and lack of coverage for new grey hair can be annoying, and by the time they do get to the salon to have it retouched, they have a grey band that is difficult to camouflage with temporary color that is available currently.

There is a gap in products for those people who want to cover or retouch grey hair in between salon visits. Some feel as though they have to go to the salon every 2-5 weeks to retouch their grey hair, depending on how fast their hair grows. In addition, frequent retouching with permanent color is not good for hair and it is also very expensive over time.

Often clients use a temporary method for covering grey hair in between retouches to try to camouflage the grey band of demarcation. These temporary methods come in different forms. There are products that can—on a very temporary basis—cover some grey hair. They could be a liquid, powder, or a cream and are applied by spray, mascara or lip gloss-type wand, or sprinkle/eyeshadow-type applicator for powder shadow. All of the available temporary cover ups only stay on your hair until your next shampoo.

These temporary methods are also a problem when you sweat. The color can run down your face and get on your clothes and pillowcase. They are also time consuming to apply, and each time you shampoo you have to reapply. If you need to shampoo your hair and you want to conceal your grey, you have to build in time to reapply your root cover up.

When a consumer wants to update his or her hair or try a new color, the options can be overwhelming. However, the ultimate goal is to apply a color for a short period of time, wherein the application is straight-forward and the result is reliable. Another goal would be for the product to be natural and naturally removed with no harsh or toxic chemicals.

To that end, a new hair coloring composition needs to be developed that ideally allows a consumer to color hair on his or her body, including his or her hair on his or her head, eyebrows, eyelashes, etc. for a fixed period of time, while at the same time allowing the consumer to apply and remove the color in a safe and natural way.

SUMMARY OF THE SUBJECT MATTER

Removable hair coloring compositions are described herein that include: at least one hair color composition or compound; and at least one sealing component or compound, wherein at least one of the at least one hair color composition or compound, or the at least one sealing component or compound can be physically dissolved, physically removed, or a combination thereof when mixed with at least one natural oil. In some embodiments, removable hair coloring compositions further include at least one preparation stage component or compound.

In some embodiments, the at least one hair color composition or compound, and the at least one sealing component or compound are separate and independent components are combinable into one removable hair coloring composition. In other embodiments, the at least one hair color composition or compound, and the at least one sealing component or compound are combined into the removable hair coloring composition before application.

In other embodiments, the at least one preparation stage component or compound, the at least one hair color composition or compound, and the at least one sealing component or compound are separate and independent components that may be combinable into the removable hair coloring composition or may be used independently of one another as part of application. In yet other embodiments, the at least one preparation stage component or compound, the at least one hair color composition or compound, and the at least one sealing component or compound are combined into the removable hair coloring composition before application.

Methods of utilizing a removable hair coloring compositions are described herein and include: applying at least one preparation stage component to at least part of at least one strand of hair; applying at least one hair color composition to at least part of at least one strand of hair; and applying at least one sealing component to the hair color composition on the at least part of at least one strand of hair, wherein at least one of the preparation stage component or compound, the hair color composition or compound, the sealing component or compound, or a combination thereof can be physically removed when mixed with a natural oil.

In addition, methods of utilizing a removable hair coloring composition include: applying at least one preparation stage component to at least part of at least one strand of hair; and applying at least one hair color composition and at least one sealing component to at least part of at least one strand of hair, wherein at least one of the preparation stage component or compound, the hair color composition or compound, the sealing component or compound, or a combination thereof can be physically removed when mixed with a natural oil.

In some embodiments, the at least one of the at least one preparation stage component or compound, the at least one hair color composition or compound, the at least one sealing component, or a combination thereof, is applied to the entirety at least one strand of hair, including grey hair.

In other embodiments, the at least one preparation stage component, the at least one hair color composition and the at least one sealing component are combined together before applying to at least part of at least one strand of hair.

BRIEF DESCRIPTION OF THE FIGURES

FIG. 3 shows a contemplated method for utilizing a removable hair coloring composition or compound.

DETAILED DESCRIPTION

The reason these contemplated embodiments and products were created was that they could be applied once, not be affected by sweat or water, and not come out off until you take it off with a remover that is gentle to the hair and scalp. This task of annoying maintenance with available products is akin to the annoyance of having to frequently reapply lipstick. Originally, contemplated embodiments were considered primarily for the coverage of grey hair and/or undesirable natural hair that grew in between touch-ups or hair colorings, but contemplated embodiments can be utilized in a number of hair applications that will be disclosed herein.

To this end, a new hair coloring composition has been developed that allows a consumer to color any hair on his or her body, including his or her head hair, eyebrows, eyelashes, etc. for a fixed period of time, while at the same time beneficially allowing the consumer to apply and remove the color in a safe and natural way.

As used herein, the phrase "removable hair coloring composition" refers to the combination of at least one hair color composition or compound; and at least one sealing component or compound, and in some embodiments, the combination of at least one preparation stage component, at least one hair color composition or compound; and at least one sealing component or compound. The phrase "hair color composition" refers to one component of the hair coloring composition, wherein the hair color composition comprises the components that are designed to apply hair color or dye to at least one strand of hair.

Figure 1:
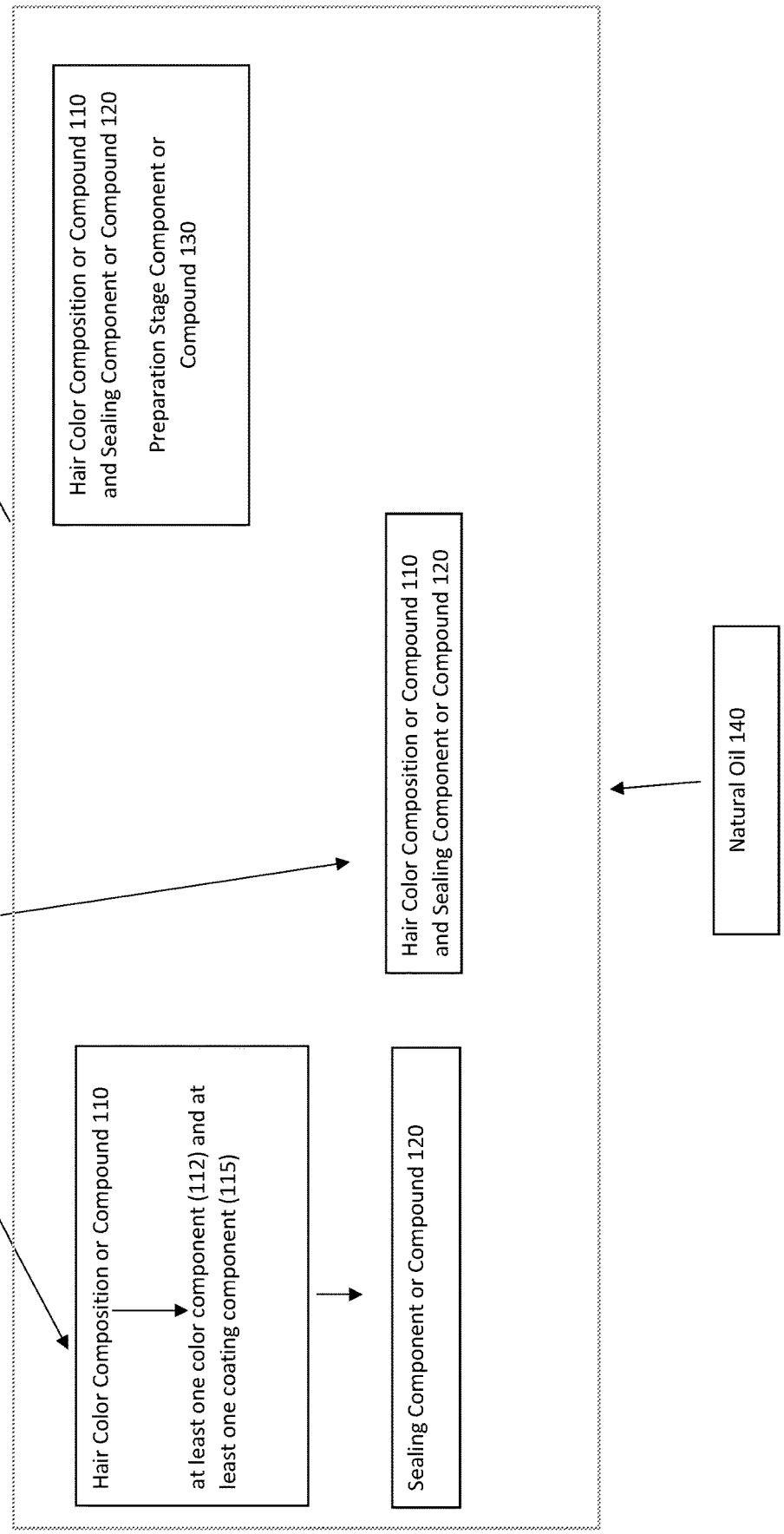
FIG. 1 shows a flow chart of a removable hair coloring composition or compound

Specifically, removable hair coloring compositions are described herein and are shown in FIG. 1 that include: at least one hair color composition or compound 110; and at least one sealing component or compound 120, wherein at least one of the at least one hair color composition or compound, or the at least one sealing component or compound can be physically dissolved, physically removed, or a combination thereof when mixed with at least one natural oil. In some embodiments, removable hair coloring compositions further include at least one preparation stage component or compound 130.

In some embodiments also shown in FIG. 1, the at least one hair color composition or compound 110, and the at least one sealing component or compound 120 are separate and independent components are combinable into one removable hair coloring composition 100. In other embodiments, the at least one hair color composition or compound 110, and the at least one sealing component or compound 120 are combined into the removable hair coloring composition 100 before application.

In other embodiments also shown in FIG. 1, the at least one preparation stage component or compound 130, the at least one hair color composition or compound 110, and the at least one sealing component or compound 120 are separate and independent components that may be combinable into the removable hair coloring composition 100 or may be used independently of one another as part of application. In yet other embodiments, the at least one preparation stage component or compound, the at least one hair color composition or compound, and the at least one sealing component or compound are combined into the removable hair coloring composition before application.

Figure 2:
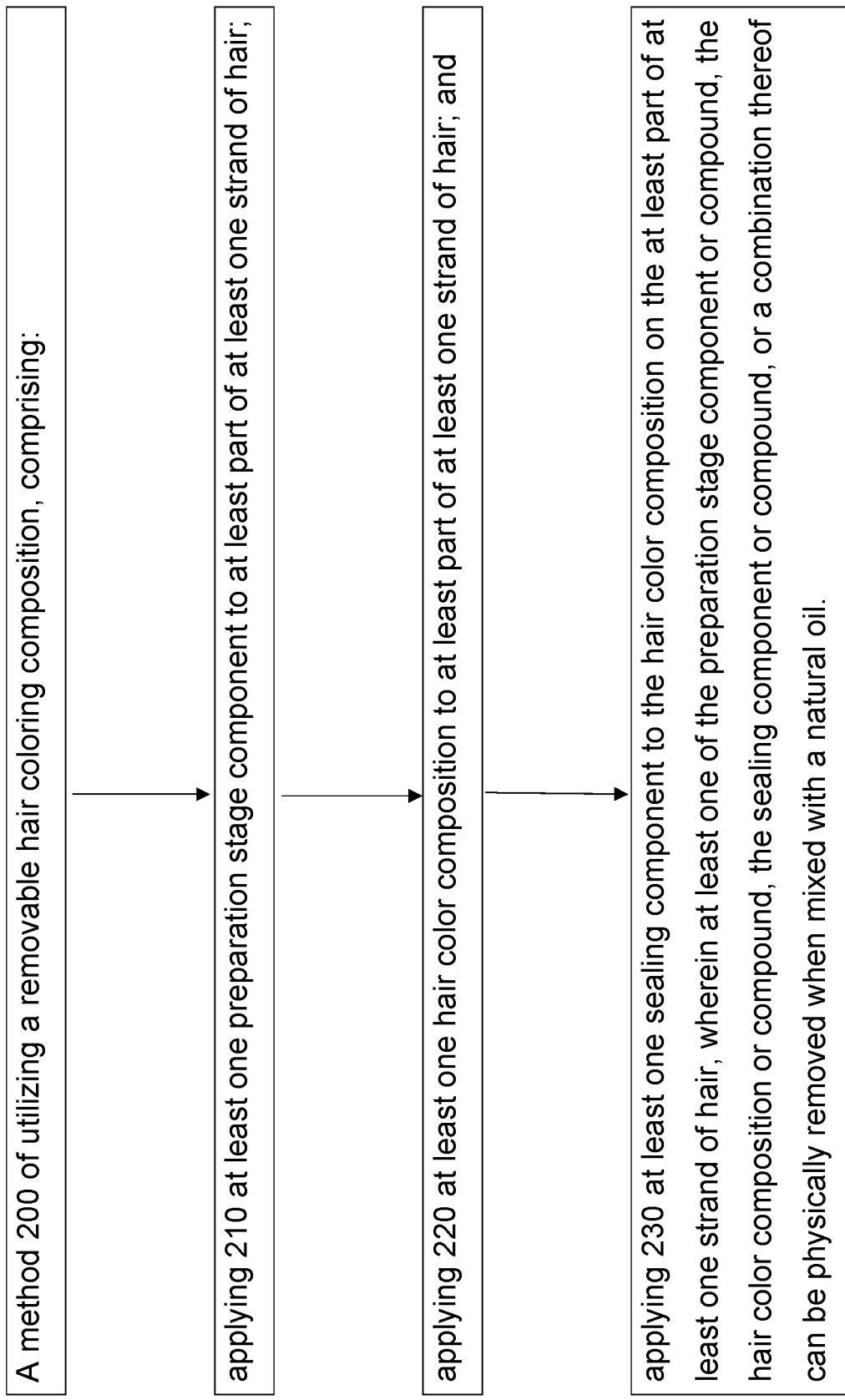
FIG. 2 shows a contemplated method for utilizing a removable hair coloring composition or compound.

Methods 200 of utilizing a removable hair coloring compositions are described herein, shown in FIG. 2 and include: applying 210 at least one preparation stage component to at least part of at least one strand of hair; applying 220 at least one hair color composition to at least part of at least one strand of hair; and applying 230 at least one sealing component to the hair color composition on the at least part of at least one strand of hair, wherein at least one of the preparation stage component or compound, the hair color composition or compound, the sealing component or compound, or a combination thereof can be physically removed when mixed with a natural oil, shown in FIG. 1 as 140.

In addition, methods 300 of utilizing a removable hair coloring composition are shown in FIG. 3 include: applying 310 at least one preparation stage component to at least part of at least one strand of hair; and applying 320 at least one hair color composition and at least one sealing component to at least part of at least one strand of hair, wherein at least one of the preparation stage component or compound, the hair color composition or compound, the sealing component or compound, or a combination thereof can be physically removed when mixed with a natural oil.

In some embodiments, the at least one of the at least one preparation stage component or compound, the at least one hair color composition or compound, the at least one sealing component, or a combination thereof, is applied to the entirety at least one strand of hair, including grey hair.

In other embodiments, the at least one preparation stage component, the at least one hair color composition and the at least one sealing component are combined together before applying to at least part of at least one strand of hair.

As contemplated herein, the at least one preparation stage component comprises at least one constituent that is designed to prepare the hair for application of a color composition or product. In some contemplated embodiments, the at least one preparation stage component comprises a constituent designed to clean the hair of any dirt, residual or undesirable oil, previously applied hair product, or the like. In some contemplated embodiments, the at least one preparation stage component comprises a constituent that is designed to apply a layer or material to the hair to allow the hair to better receive, capture, or hold on to the at least one color composition. In yet other embodiments, these two sets of constituents may be included in the at least one preparation stage component and would be designed to work together to prepare the hair or portion of the hair for application of the at least one color composition or compound.

Contemplated hair color compositions comprise materials and constituents that can be dissolved in and/or removed from hair by a natural oil, such as coconut oil, avocado oil, nut oil, or something similar. The hair color is designed to coat or cover strands or follicles of hair until the color coating is removed with the application of a natural oil or a product that contains a natural oil, such as a specially designed spray or shampoo. Contemplated color coatings or compositions may be designed to cover grey hair or lessen the effects of grey hair; may change the color of the hair entirely, such as from blond to brown or red; may enhance an already existing hair color, such as from light brown to dark brown; and/or may add an "on trend" color, such as green, purple, or blue to the existing hair.

Specifically, a contemplated hair color composition comprises at least one color component 112 and at least one coating component 115. A contemplated coating component is one that can—alone or in combination with other coating components—reliably secure the at least one-color component to a hair follicle until a natural oil is applied. In some embodiments, however, a sealing component or composition would or could be applied to the hair as a second step to seal in the color component. In some embodiments, this contemplated sealing component or composition may be incorporated into the hair color composition.

It should also be understood that the at least one color component isn't designed in contemplated compositions to permanently alter the color of the hair. Contemplated color components may permanently alter the color of the hair in other compositions—but in contemplated compositions, the at least one-color component is designed to be coated on the hair and removed by application of a natural oil. When the at least one-color component is removed, the hair looks as it did before application.

While this subject matter was originally developed to cover grey hair and grey hair roots, contemplated hair color compositions are designed to be applied to all types of hair, including hair that grows from the scalp, eyebrows, eyelashes, and body hair. These compositions are also designed for all kinds of hair, including straight hair, curly hair, thin hair, thick hair—all of it.

Methods of application and removal of contemplated hair color compositions are also included herein. In some embodiments, a contemplated application method includes applying a preparation stage component; applying a hair color composition; and applying a sealing component. In some embodiments, the preparation stage component may include a shampoo or co-wash (conditioner wash) component. In some contemplated embodiments, the applying of a hair color composition and the applying of a sealing component may be combined into one step.

In some embodiments, a contemplated removal method includes applying a pre-removal stage component; applying a removal stage component; and applying a conditioning component. In some embodiments, the pre-removal stage component may include a shampoo or co-wash (conditioner wash) component that may include a natural oil, such as coconut oil, avocado oil, nut oil, or something similar. In some embodiments, the removal stage component comprises a natural oil, such as coconut oil, avocado oil, nut oil, or something similar. In some contemplated embodiments, the applying of a pre-removal composition and the applying of a removal stage component may be combined into one step.

Thus, specific embodiments, methods of producing and using removable hair coloring compositions have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A removable hair coloring composition, comprising:
    at least one hair color composition or compound; and
    at least one sealing component or compound, wherein each of the at least one hair color composition or compound, or the at least one sealing component or compound can be physically dissolved, physically removed, or a combination thereof when mixed with at least one natural oil.

2. The removable hair coloring composition of claim 1, further comprising at least one preparation stage component or compound.

3. The removable hair coloring composition of claim 1, wherein the at least one hair color composition or compound comprises:
    at least one color component; and
    at least one coating component.

4. The removable hair coloring composition of claim 1, wherein the at least one hair color composition or compound, and the at least one sealing component or compound are separate and independent components that are combinable into one removable hair coloring composition.

5. The removable hair coloring composition of claim 1, wherein the at least one hair color composition or compound, and the at least one sealing component or compound are combined into the removable hair coloring composition before application.

6. The removable hair coloring composition of claim 2, wherein the at least one preparation stage component or compound, the at least one hair color composition or compound, and the at least one sealing component or compound are separate and independent components that may be combinable into the removable hair coloring composition or may be used independently of one another as part of application.

7. The removable hair coloring composition of claim 2, wherein the at least one preparation stage component or compound, the at least one hair color composition or compound, and the at least one sealing component or compound are combined into the removable hair coloring composition before application.

8. The removable hair coloring composition of claim 1, wherein the at least one natural oil comprises coconut oil, avocado oil, nut oil, or a combination thereof.

9. A method of utilizing a removable hair coloring composition, comprising:
    applying at least one preparation stage component to at least part of at least one strand of hair;
    applying at least one hair color composition to at least part of at least one strand of hair; and
    applying at least one sealing component to the hair color composition on the at least part of at least one strand of hair, wherein each of the preparation stage component or compound, the hair color composition or compound, the sealing component or compound, or a combination thereof can be physically removed when mixed with a natural oil.

10. A method of utilizing a removable hair coloring composition, comprising:
applying at least one preparation stage component to at least part of at least one strand of hair; and
applying at least one hair color composition and at least one sealing component to at least part of at least one strand of hair, wherein each of the preparation stage component or compound, the hair color composition or compound, the sealing component or compound, or a combination thereof can be physically removed when mixed with a natural oil.

11. The method of claim 9, wherein the at least one of the at least one preparation stage component or compound, the at least one hair color composition or compound, the at least one sealing component, or a combination thereof, is applied to the entirety at least one strand of hair.

12. The method of claim 10, wherein the at least one of the at least one preparation stage component or compound, the at least one hair color composition or compound, the at least one sealing component, or a combination thereof, is applied to the entirety at least one strand of hair.

13. The method of claim 9, wherein the at least one strand of hair is grey hair.

14. The method of claim 10, wherein the at least one strand of hair is grey hair.

15. The method of claim 9, wherein the at least one preparation stage component, the at least one hair color composition and the at least one sealing component are combined together before applying to at least part of at least one strand of hair.

16. The method of claim 10, wherein the at least one preparation stage component, the at least one hair color composition and the at least one sealing component are combined together before applying to at least part of at least one strand of hair.

* * * * *